United States Patent [19]

Aleshin et al.

[11] Patent Number: 5,060,518
[45] Date of Patent: Oct. 29, 1991

[54] METHOD OF ULTRASONIC INSPECTION OF WELDS OF ARTICLES

[75] Inventors: Nikolai P. Aleshin; Vladimir J. Baranov, both of Moscow; Leonid J. Mogilner, Moskovskaya; Alexandr A. Yarovoi, Nikolaev, all of U.S.S.R.

[73] Assignee: Moskovskoe Vysshee Tekhnicheskoe Uchilische Imeni N.E. Baumana, Moscow, U.S.S.R.

[21] Appl. No.: 460,908
[22] PCT Filed: May 20, 1988
[86] PCT No.: PCT/SU88/00112
§ 371 Date: Feb. 13, 1990
§ 102(e) Date: Feb. 13, 1990
[87] PCT Pub. No.: WO89/11651
PCT Pub. Date: Nov. 30, 1989
[51] Int. Cl.$^5$ ............................................. G01N 29/10
[52] U.S. Cl. ........................................ 73/620; 73/627
[58] Field of Search ............... 73/602, 614, 619, 624, 73/620, 627

[56] References Cited

U.S. PATENT DOCUMENTS

| 3,552,191 | 1/1971 | Heseding | 73/625 |
| 4,289,030 | 9/1981 | Alers et al. | 73/643 |
| 4,679,437 | 7/1987 | Koike et al. | 73/622 |
| 4,805,459 | 2/1989 | Ferreira | 73/627 |

FOREIGN PATENT DOCUMENTS

| 2840456 | 3/1980 | Fed. Rep. of Germany . | |
| 6044618 | 4/1978 | Japan . | |
| 6042415 | 10/1979 | Japan . | |
| 461361 | 2/1975 | U.S.S.R. . | |
| 855487 | 8/1981 | U.S.S.R. . | |
| 1067432 | 1/1984 | U.S.S.R. . | |
| 1165981 | 7/1985 | U.S.S.R. | 73/627 |
| 2151786 | 7/1985 | United Kingdom . | |

OTHER PUBLICATIONS

"Flaw Classification by a Spectral Division of Ultrasonic Echos", by H. Seiger and T. Wagner (Not International, vol. 16, No. 4, 8/83).

Primary Examiner—Hezron E. Williams
Assistant Examiner—Rose M. Finley
Attorney, Agent, or Firm—Ladas & Parry

[57] ABSTRACT

The method of ultrasonic inspection of welds of articles, wherein planes (3, 8) of polarization of transverse ultrasonic oscillations radiated into a weld (4) of an article (2) and of these oscillations registered upon their reflection by the reflecting surface of a flaw (6) of the weld (4) are set relative to each other at an angle $2\delta$, an angle $\xi_1$ between the plane (3) of polarization and a plane (5) of incidence of ultrasonic oscillations upon the reflecting surface and an angle $\xi_2$ between the plane (8) of polarization and the plane (5) of incidence being selected substantially equal to 70°, thus providing for extracting from the radiated ultrasonic oscillations their component polarized horizontally with respect to the reflecting surface of the flaw (6), the amplitude of which is employed to estimate the geometrical parameters of the flaw (6), while the time of its registration is used to estimate the location of the flaw (6) in the weld (4).

2 Claims, 8 Drawing Sheets

METHOD OF ULTRASONIC INSPECTION OF WELDS OF ARTICLES

TECHNICAL FIELD

The present invention relates to methods of nondestructive testing and inspection of articles, and, more particularly, it relates to methods of ultrasonic inspection of welds of articles.

BACKGROUND ART

There is known a method of ultrasonic inspection of articles, including the steps of selecting parallel directions of transverse ultrasonic oscillations radiated into an article and of transverse oscillations mirror-reflected by the reflecting surface of a flaw of a weld of the article and by the surface of the article, these directions belonging to the planes of polarization of the radiated and registered transverse oscillations, coinciding with one another and with the plane of incidence of these oscillations upon the reflecting surface of the flaw of the weld of the article, and intermittently radiating into the article transverse ultrasonic oscillations and registering transverse oscillations reflected by the reflecting surface of the flaw and by the surface of the article, for evaluating the geometrical parameters of the flaw (SU, A, 461361).

According to this method, the transverse oscillations incident upon the reflecting surface of the flaw are vertically polarized with respect to this surface. These oscillations are transformed into other kinds of oscillations, e.g. longitudinal oscillations, when their angle of incidence upon the reflecting surface of the flaw is either close to or short of the third critical angle. In this case the reflection factor of the transverse oscillations by the reflecting surface of the flaw sharply drops, and at the same time the interference caused by other kinds of ultrasonic oscillations is reinforced. Consequently, both the sensitivity of ultrasonic inspection in accordance with this known method and its immunity to interference are relatively low, which can be vividly seen in its implementation for inspection of welds of articles of relatively small thickness (below 30 mm).

Besides the low sensitivity and immunity to interference of this known method, it is further characterized by the necessity, in its implementation for inspection of welds of articles thinner than 30 mm, of arranging the piezoelectric transducers employed for radiating and registering the ultrasonic oscillations very close to one another on the surface of the article, which is not always possible on account of the own geometric dimensions of the piezoelectric transducers themselves.

There is further known a method of ultrasonic inspection of welds of articles, including the steps of specifying the direction of radiating transverse ultrasonic oscillations into an article, the plane of polarization of transverse ultrasonic oscillations radiated into a weld of the article, the plane of their incidence upon the reflecting surface of a flaw of the weld of the article, the direction of mirror reflection of these oscillations by the reflecting surface of the flaw of the weld of the article and the plane of polarization of transverse ultrasonic oscillations registered upon their mirror reflection by the reflecting surface of the flaw of the weld, and intermittently radiating transverse ultrasonic oscillations into the article and registering the transverse ultrasonic oscillations reflected by the reflecting surface of the weld of the article, for evaluating the geometric parameters of the flaw (SU, A, 855487).

According to this method, the transverse ultrasonic oscillations radiated into the article contain components which are both vertically and horizontally polarized with respect to the reflecting surface of the flaw of the weld of the article. This is attained owing to the respective directions of radiating transverse ultrasonic oscillations and their mirror reflection being symmetrical with respect to a plane perpendicular to the longitudinal axis of the weld and including the flaw.

However, the ratio of the amplitudes of these respective components is such that the amplitude of the vertically polarized component tends to be significantly greater. This results in a reduced amplitude of transverse oscillations reflected by the flaw, the growing amplitude of transformed longitudinal oscillations and, consequently, in impaired sensitivity and immunity to interference of the ultrasonic inspection procedure, i.e. to adversely affected credibility of the outcome of the inspection.

Furthermore, the last-described known method would not be implemented for ultrasonic inspection of pipes of diameters in excess of 100 mm and of flat articles, since in such cases it would be impossible to maintain the directions of radiation and registration of ultrasonic oscillations, required by the method.

DISCLOSURE OF THE INVENTION

The object of the present invention is to create a method of ultrasonic inspection of welds of articles, wherein a novel arrangement of the planes of polarization of transverse ultrasonic oscillations radiated into a weld of an article and of the ultrasonic oscillations registered upon their reflection by the reflecting surface of the flaw of the weld of the article would make it possible to extract from the oscillations after their mirror reflection by the reflecting surface of the flaw those components which would allow enhancing the sensitivity and the immunity to interference in ultrasonic inspection of welds in a wider range of inspected articles and, in effect, increasing its reliability and including into the wider range of articles pipes over 100 mm in diameter and flat elements.

These and other objects are attained by providing a method of ultrasonic inspection of welds of articles, including the steps of specifying the direction of radiation of transverse ultrasonic oscillations into the article, a plane of polarization of the transverse ultrasonic oscillations radiated into the weld, a plane of incidence of said transverse ultrasonic oscillations upon the reflecting surface of a flaw in the weld of the article, a direction of mirror reflection of these oscillations from the reflecting surface of the welding flaw of the article and a plane of polarization of the transverse ultrasonic oscillations being registered after the mirror reflection from the reflecting surface; the above-said planes of polarization of the transverse ultrasonic oscillations radiated into the weld of the article and registered after they have been reflected from said reflecting surface of the flaw of the weld of the article are disposed relative to each other at a preset angle of 2δ; determining this angle by disposing the direction of radiation of the oscillations into the weld and the direction of mirror reflection of these oscillations from the reflecting surface outside the plane perpendicular to the longitudinal axis of the weld and extending through said reflecting surface of said flaw and by selecting the angle between the plane of polarization of the transverse ultrasonic oscillations radiated into the weld of the article and the plane of incidence of the ultrasonic oscillations onto the reflecting surface and the angle $\xi_2$ between the plane of polarization of the transverse ultrasonic oscillations being registered after their reflection from the reflecting surface of the flaw and the plane of incidence of these ultrasonic oscillations on the reflecting surface of the flaw, either equal or in excess of 64° but less than 90°, thus extracting from the transverse ultrasonic oscillations a component horizontally polarized relative to the reflecting surface; periodic radiation of the transverse ultrasonic oscillations into the article and registration of the oscillations reflected from the reflecting surface; using the horizontally polarized component extracted from the oscillations for estimation of the geometric size of the flaw, namely, the amplitude of the horizontally polarized component is used for estimation of the geometric size of the flaw while the time of its registration is used for location the flaw in the weld.

It is expedient that the angle $2\delta$ between the respective planes of polarization of the transverse ultrasonic oscillations radiated into the weld of the article and of the ultrasonic oscillations registered upon their reflection by the reflecting surface of the weld should be specified by arranging the respective directions of radiating transverse ultrasonic oscillations into the article and of mirror reflection of these ultrasonic oscillations by the reflecting surface of the flaw of the weld of the article outside a plane perpendicular to the longitudinal axis of the weld of the article and intersecting the reflecting surface of the flaw of the weld.

In cases of ultrasonic inspection of welds of articles having a planar surface through which transverse ultrasonic oscillations are radiated into the article and registered upon their reflection by the reflecting surface of a flaw of the weld of the article, and a surface of arbitrary shape opposite to this first-mentioned surface, it is expedient that the angle $\xi_1$ between the plane of polarization of the transverse ultrasonic oscillations radiated into the weld of the article and the plane of incidence of these ultrasonic oscillations upon the reflecting surface of the flaw of the weld of the article and the angle $\xi_2$ between the plane of polarization of the transverse ultrasonic oscillations registered upon their reflection by the reflecting surface of the flaw of the weld of the article and the plane of incidence of these ultrasonic oscillations upon the reflecting surface of the flaw of the weld should be equal, i.e. $\xi_1 = \xi_2 = \xi$, and that the angle $2\delta$ between the respective planes of polarization of the transverse ultrasonic oscillations radiated into the article and of the ultrasonic oscillations registered upon their reflection by the reflecting surface of the flaw of the weld of the article should be selected from an expression $$2\delta = 2 \arccos \frac{1}{\sqrt{1 + \cos^2\alpha \tan^2\xi}} \quad /1/$$

or $$2\delta = 2 \arcsin \frac{1}{\sqrt{1 + \cos^2\alpha \tan^2\xi}} \quad /2/$$

where $\alpha$ is the angle between the direction of radiating transverse ultrasonic oscillations into the article and a line normal to the first-mentioned surface of the article, equalling the angle $\alpha$ between the direction of mirror reflection of these ultrasonic oscillations by the reflecting surface of the flaw of the weld and the line normal to said first-mentioned surface of the article.

The disclosed method of ultrasonic inspection of welds of articles provides for enhancing the sensitivity and interference immunity of ultrasonic inspection of welds of articles owing to the registration of that component of the transverse ultrasonic oscillations incident upon the reflecting surface of the flaw of the article, which is horizontally polarized with respect to this surface, a factor increasing the amplitude of the ultrasonic oscillations reflected by the reflecting surface of the flaw of the weld and reducing the amplitude of ultrasonic oscillations transformed at the reflecting surface of the flaw of the article and generating ultrasonic noise. In this way the credibility of detection of flaws in ultrasonic inspection of welds of articles is enhanced, which is of paramount importance in detection of three-dimensional or "spatial" flaws of weld welds of articles, e.g. pores or slag inclusions.

Furthermore, the disclosed method of ultrasonic inspection of welds of articles provides for "sounding out" a flaw of a weld of an article from different sides and, by comparing the amplitudes of ultrasonic oscillations reflected by the reflecting surface of the flaw in different directions, for determining the shape of the flaw, i.e. for distinguishing between "spatial" and "planar" flaws, and also for determining their orientation in the weld of the article.

The method of ultrasonic inspection of welds of articles in accordance with the invention provides for defining the optimized parameters of ultrasonic inspection of articles including those of thicknesses short of 30 mm, by selecting appropriately the angle $2\delta$ between the respective planes of polarization of radiated and reflected ultrasonic oscillations, different from zero. This enables one to arrange the piezoelectric transducers on the surfaces of inspected articles in a convenient manner, pipes of diameters in excess of 100 mm and flat articles included.

BRIEF DESCRIPTION OF THE DRAWINGS

The invention will be further described in connection with its embodiments, with reference being made to the accompanying drawings, wherein.

BEST MODE OF CARRYING OUT THE INVENTION

Figure 1:
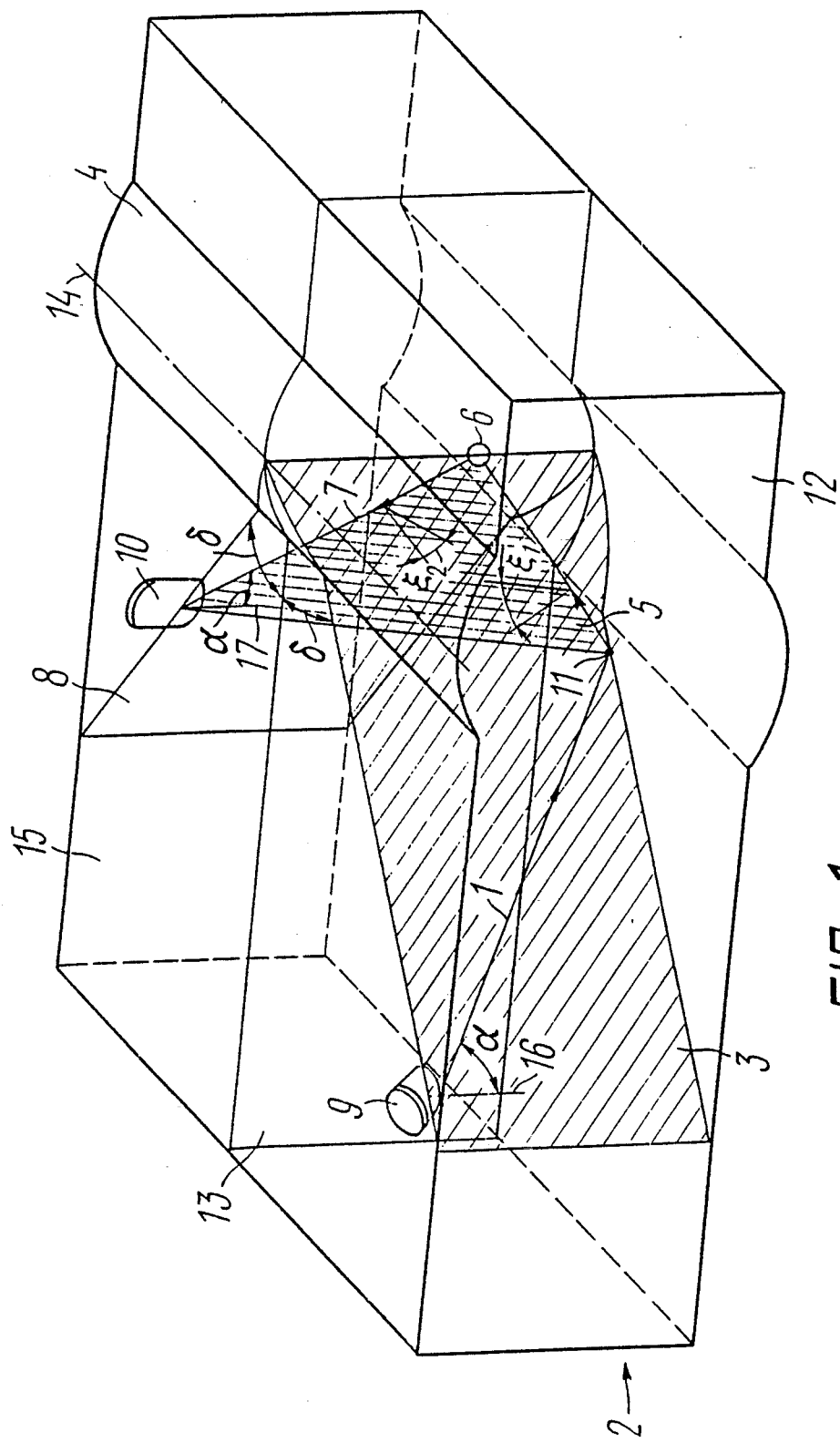
FIG. 1 illustrates schematically in a perspective view an arrangement for implementing a method of ultrasonic inspection of welds of articles, embodying the invention.

In the method of ultrasonic inspection of welds of articles embodying the present invention there are defined, first, the direction 1 (FIG. 1) of radiating transverse ultrasonic oscillations into an article 2, the plane 3 of polarization of the ultrasonic transverse oscillations radiated into the weld 4 of the article 2 (the plane 3 is shaded in the drawing of FIG. 1 for clarity sake). the plane 5 of incidence of these oscillations upon the reflecting surface of a flaw 6 of the weld 4 of the article 2 (the plane is likewise shaded in the drawing of FIG. 1 for better clarity, differently from the shading of the plane 3), the direction 7 of mirror reflection of these ultrasonic oscillations by the reflecting surface of the flaw 6 of the weld 4, and the plane 8 of polarization of the transverse ultrasonic oscillations registered upon their mirror reflection by the reflecting surface of the flaw 6. For better clarity, the article 2 is conditionally regarded transparent.

The respective planes 3 and 8 of polarization of the transverse ultrasonic oscillations radiated into the weld 4 of the article 2 and of the ultrasonic oscillations registered upon their reflection by the reflecting surface of the flaw 6 of the weld 4 are arranged relative to each other at a specified angle $2\delta$. There are also selected the angle $\xi_1$ between the plane 3 of polarization of transverse ultrasonic oscillations radiated into the weld 4 of the article 2 and the plane 5 of incidence of these ultrasonic oscillations upon the reflecting surface of the flaw 6 of the weld 4, and the angle $\xi_2$ between the plane 8 of polarization of the transverse ultrasonic oscillations registered upon their reflection by the reflecting surface of the flaw 6 of the weld 4 and the plane 5 of incidence of these ultrasonic oscillations upon the reflecting surface of the flaw 6, either equal to or in excess of 64°, but short of 90°, thus providing for extracting from the radiated transverse ultrasonic oscillations their component polarized horizontally with respect to the reflecting surface of the flaw 6.

The ratio of the amplitudes of the horizontally and vertically polarized components of the transverse ultrasonic oscillations incident upon the reflecting surface of the flaw 6 equals $\tan \xi_1$. Thus, when the angle $\xi_1$ is selected within the abovementioned range, the ratio of the amplitudes of the horizontally and vertically polarized components in the transverse ultrasonic oscillations incident upon the reflecting surface of the flaw 6 is 2:1 or more, i.e. 6 dB or more. If the angle $\xi_2$ is also within this range, the first-mentioned component can be reliably extracted independently of the second-mentioned one.

Figure 2:
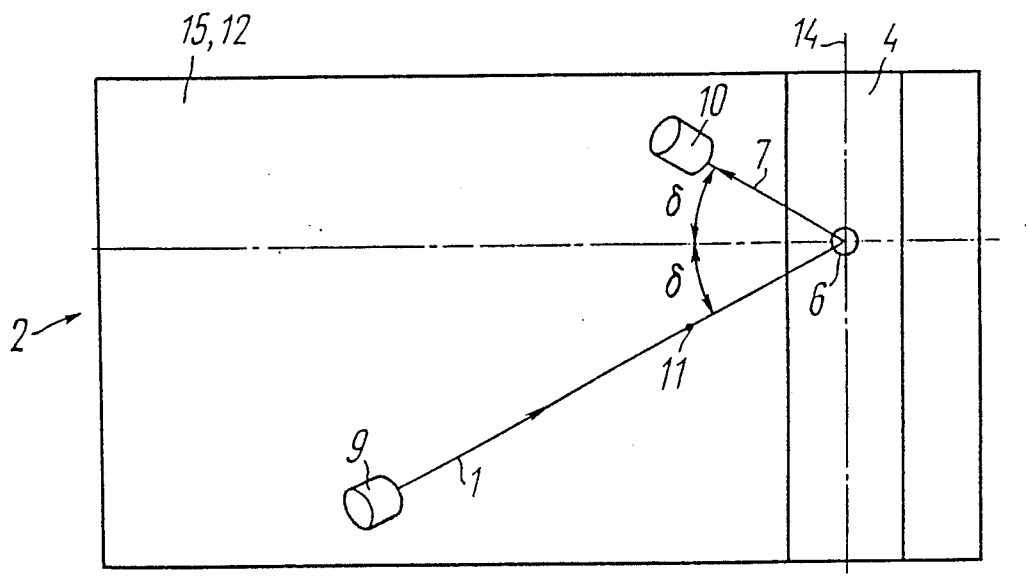
FIG. 2 is a view in plan on a smaller scale of the arrangement of FIG. 1.
Figure 3:
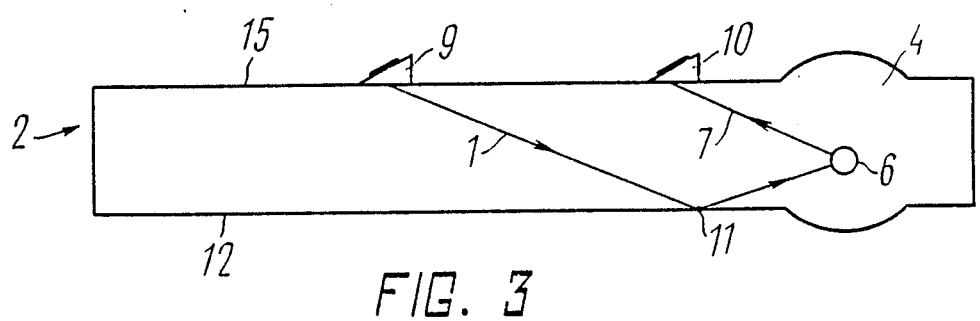
FIG. 3 is a front view on a smaller scale of the arrangement of FIG. 1.

Then an ultrasonic piezoelectric transducer 9 (FIGS. 1 to 3) is intermittently operated to radiate transverse ultrasonic oscillations into the article 2, and another ultrasonic piezoelectric transducer 10 is operated to receive transverse ultrasonic oscillations reflected, firstly, by the point 11 of the surface 12 of the article 2 and then by the reflecting surface of the flaw 6 of the weld 4, for evaluating the geometrical parameters (geometrical dimensions, location) of the flaw 6 of the weld 4 of the article 2.

The geometrical dimensions of the flaw 6 of the weld 2 are estimated from the registered value of the amplitude of the horizontal component, and the location of the flaw 6 in the weld 4 is found from the time of registration of this amplitude.

The angle $2\delta$ (FIG. 1) between the respective planes 3 and 8 of polarization of the transverse ultrasonic oscillation radiated into the weld 4 of the article 2 and of the oscillations registered upon their reflection by the reflecting surface of the flaw 6 of the weld 4 is defined by specifying the respective directions 1 and 7 of radiating transverse ultrasonic oscillations into the article 2 and of reflection of these ultrasonic oscillations by the reflecting surface of the flaw 6 of the weld 4 outside a plane 13 perpendicular to the longitudinal axis 14 of the weld 4 and intersecting the reflecting surface of the flaw 6 of the weld 4.

In the embodiment of the disclosed method being described, the article 2 (FIGS. 1 to 3) subjected to ultrasonic inspection has a planar surface 15 through which transverse ultrasonic oscillations are radiated into the article 2 and registered upon their reflection by the opposite surface 12 of the article 2 and by the reflecting surface of the flaw 6 of the weld 4. The surface 12 can have an arbitrary shape, and in the case being described it is parallel with the surface 15.

In this case, the respective directions 1 (FIG. 1) and 7 of radiation and reflection of transverse ultrasonic oscillations are defined at two sides of the plane 13. The angles $\xi_1$ and $\xi_1$ are equal, i.e. $\xi_1=\xi_2=\xi$, and the angle $2\delta$ is selected from the relationship:

$$2\delta = 2 \arccos \frac{1}{\sqrt{1 + \cos^2\alpha \tan^2\xi}} \quad /3/$$

where $\alpha$ is the angle between the direction 1 of radiation of transverse ultrasonic oscillations into the article 2 and a line 16 normal to the surface 15 of the article 2, equalling the angle $\alpha$ between the direction 7 of mirror reflection of these ultrasonic oscillaions by the reflecting surface of the flaw 6 of the weld 4 and a line 17 normal to the surface 15.

Let us consider as an example of implementation of the disclosed method the detection of the flaw 6 (FIGS. 1 to 3) —a spherical pore in the weld 4 of the article 2 made of steel, with $\alpha=70°$.

Figure 4:
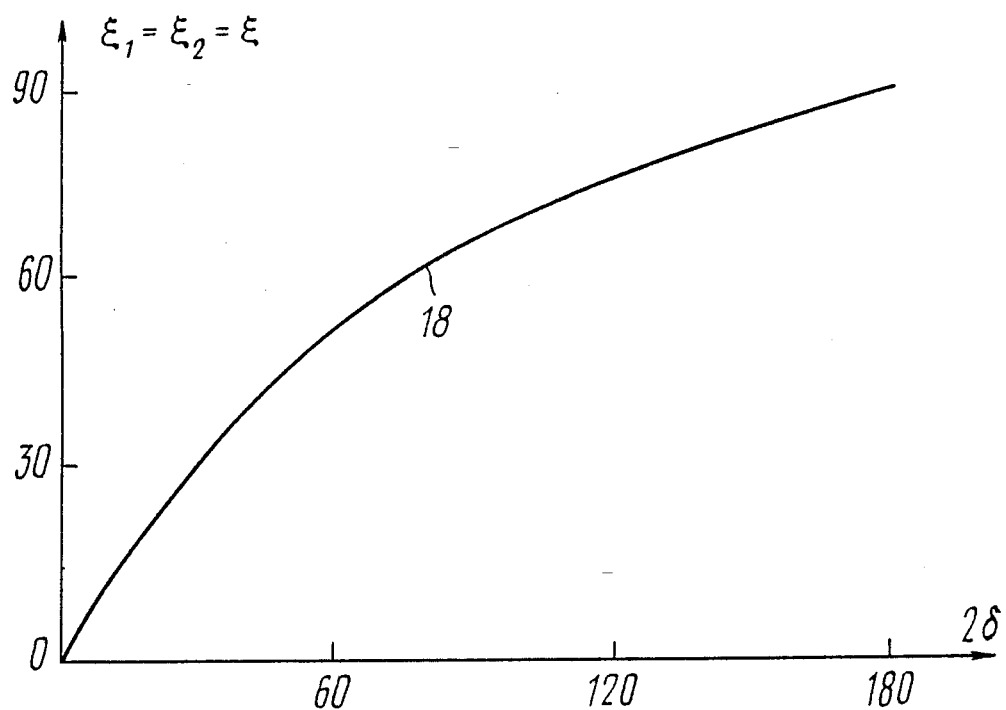
FIG. 4 presents a plot of dependence of the angle $\xi_1$ between the plane of polarization of transverse ultrasonic oscillations radiated into the weld of the article and the plane of incidence of these iscillations upon the reflecting surface of a flaw (or of the equal angle $\xi_2$ between the plane of polarization of the transverse ultrasonic oscillations registered upon their reflection by the reflecting surface of the flaw and the plane of incidence of these oscillations upon the reflecting surface of the flaw, i.e. $\xi_1 = \xi_2 = \xi$) on the angle $2\delta$ between the respective planes of polarization of the transverse ultrasonic oscillations radiated into the weld of the article and registered upon their reflection by the reflecting surface of the flaw, in the arrangement of FIGS. 1 to 3.
Figure 5:
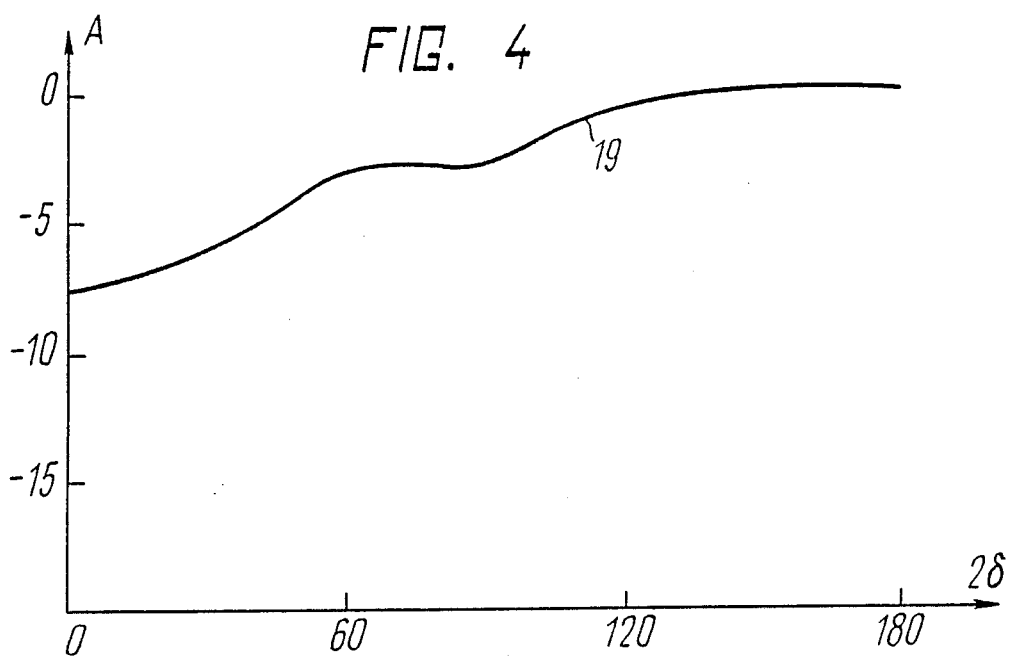
FIG. 5 presents a plot of dependence of the amplitude A of registered ultrasonic oscillations upon the angle $2\delta$, obtained in the arrangement of FIGS. 1 to 3.

In the plots presented by FIGS. 4 and 5, the X-axis is calibrated in the values of angles $2\delta$ (in degrees). The Y-axis in FIG. 4 is calibrated in the values of the angles $\xi_1=\xi_2=\xi$ (in degrees), and the Y-axis of FIG. 5 is calibrated in the values of the amplitude A of registered transverse ultrasonic oscillations (in decibels, dB).

As it is demonstrated by the curve 18 (FIG. 4) describing the relationship between $\xi$ and $2\delta$ for the abovespecified value of $\alpha$, when the angle $\xi$ is selected in accordance with the disclosed method from the range $64° \leq \xi < 90°$, the angle $2\delta$ is selected from a range $75° \leq 2\delta < 180°$. Then the amplitude A of the horizontally polarized component of the transverse oscillations incident upon the reflecting surface of the flaw 6 (FIGS. 1 to 3) of the weld 4 of the article 2 would be at least two times greater (6 dB) than the amplitude of the vertically polarized component. Thus, it can be seen from the curve 19 in FIG. 5 that the amplitude A of the registered transverse ultrasonic oscillations exceeds by 6 dB or more the amplitude of transverse ultrasonic oscillations registered in cases where $\xi=0°$ ($2\delta=0°$).

Figure 6:
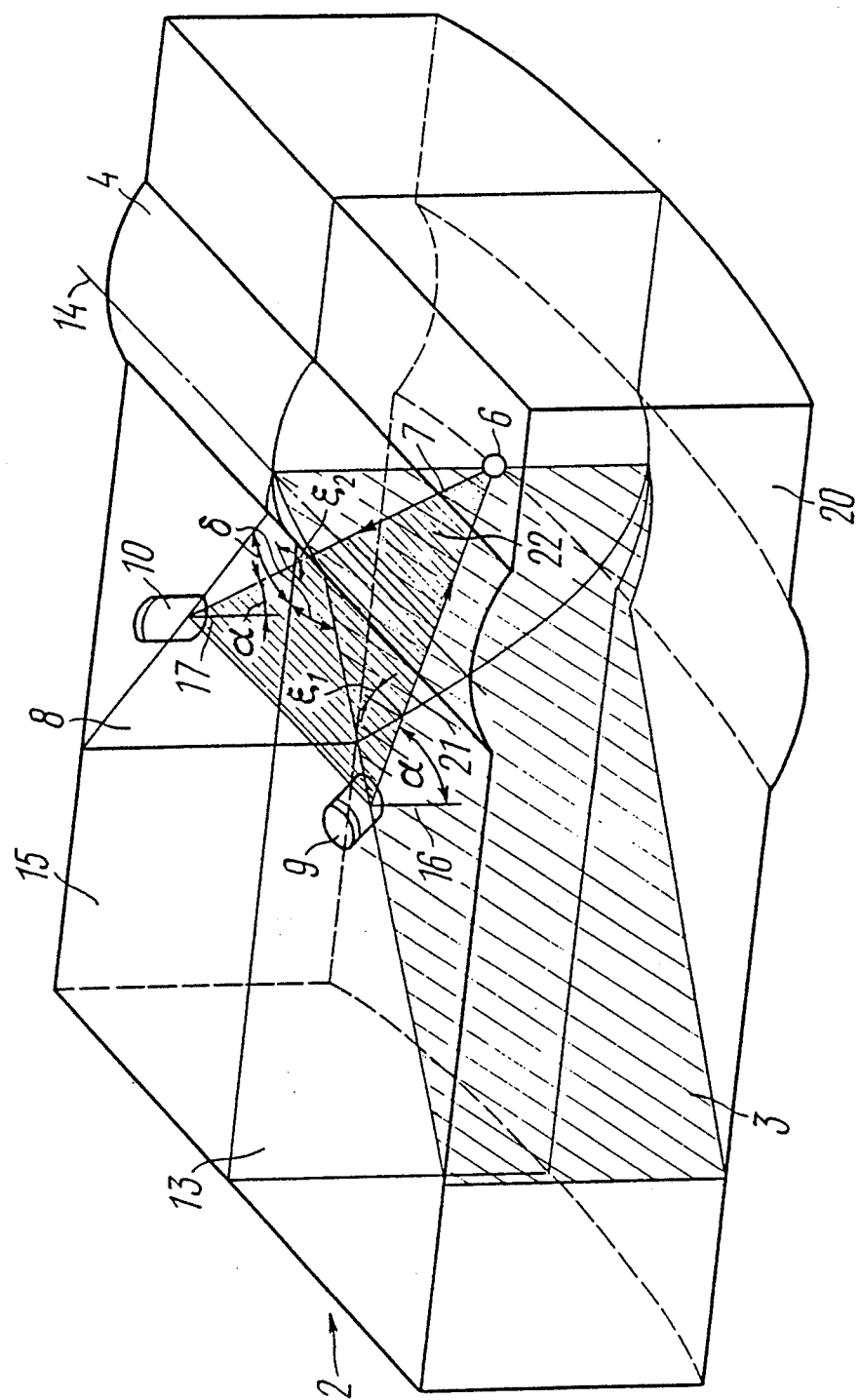
FIG. 6 illustrates schematically in a perspective view an arrangement for implementing a modified version of the method of ultrasonic inspection of welds of articles in accordance with the invention.

In another arrangement for implementing a method in accordance with the present invention, illustrated in FIG. 6, the article 2 whose weld 4 is to be inspected has a planar surface 15 through which transverse ultrasonic oscillations are radiated into the article 2 and registered upon their reflection by the reflecting surface of the flaw 6 of the weld 4, and a surface 20 opposite to the first-mentioned surface 15, having an arbitrary shape, e.g. convex as shown in FIG. 6. The method embodying the present invention is performed in this arrangement basically similarly to the method described in connection with the arrangement illustrated in FIGS. 1 to 3.

The difference is that the ultrasonic transverse oscillations radiated by the ultrasonic piezoelectric transducer 9 (FIG. 6) through the planar surface 15 of the article 2 propagate in a direction 21 and, without being reflected by the opposite surface 20 of the article 2, are reflected directly by the reflecting surface of the flaw 6 of the weld 4 of the article 2. Upon having been reflected by the flaw 6, the transverse oscillations propagate in the direction 7 and are registered by the ultrasonic piezoelectric transducer 10. The respective planes 3 and 8 of polarization of the ultrasonic oscillations radiated into the article 2 and of the registered ultrasonic oscillations retain their respective positions described above, whereas the plane 22 of incidence of the ultrasonic oscillations upon the reflecting surface of the flaw 6 of the weld 4 of the article 2 attains a different position. In this case, the angles $\xi_1$ and $\xi_2$ are also equal, i.e. $\xi_1=\xi_2=\xi$,, and the angle $2\delta$ is defined from the relationship:

$$2\delta = 2 \arcsin \frac{1}{\sqrt{1 + \cos^2\alpha \tan^2\xi}} \quad /4/$$

Let us now discuss an example of implementing the method in accordance with the invention in the detection of the flaw 6 (FIG. 6)—a spherical pore—in the weld 4 of the article 2 made of steel, with $\alpha=35°$.

Figure 7:
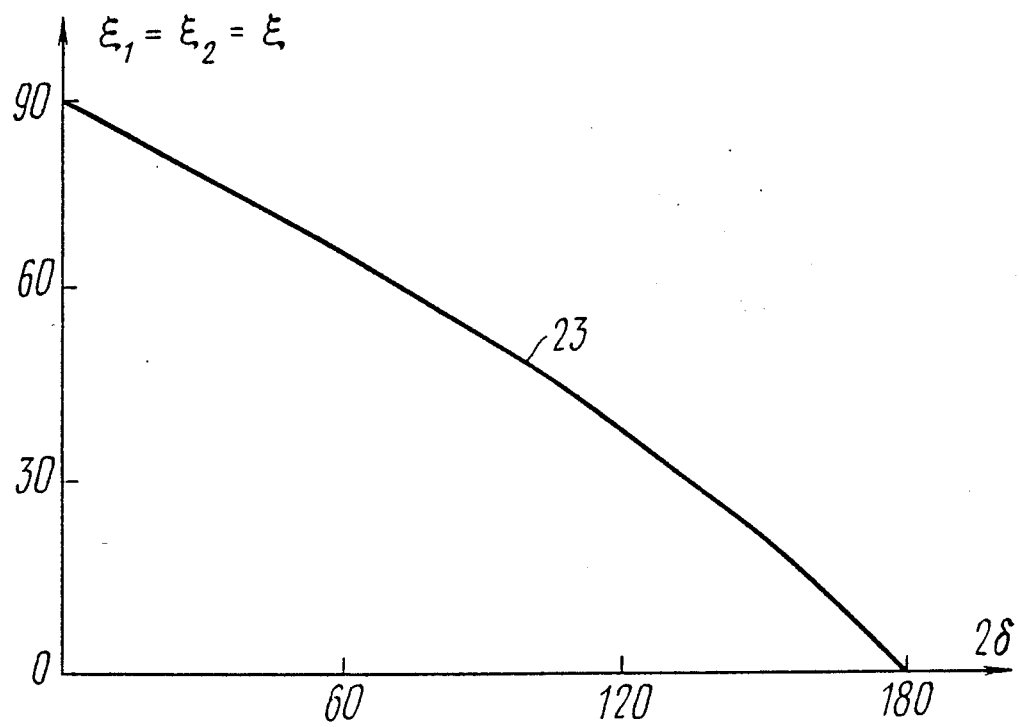
FIG. 7 presents a plot illustrating the dependence of the angle $\xi_1$ between the plane of polarization of transverse ultrasonic oscillations radiated into the weld of the article and the plane of incidence of these oscillations upon the reflecting surface of a flaw (or of the equal angle $\xi_2$ between the plane of polarization of the ultrasonic oscillations registered upon their reflection by the reflecting surface of the flaw and the plane of incidence of these oscillations upon the reflecting surface of the flaw, i.e. $\xi_1 = \xi_2 = \xi$) on the angle $2\delta$ between the respective planes of polarization of the ultrasonic oscillations radiated into the weld of the article and reflected by the reflecting surface of the flaw, in the arrangement of FIG. 6.
Figure 8:
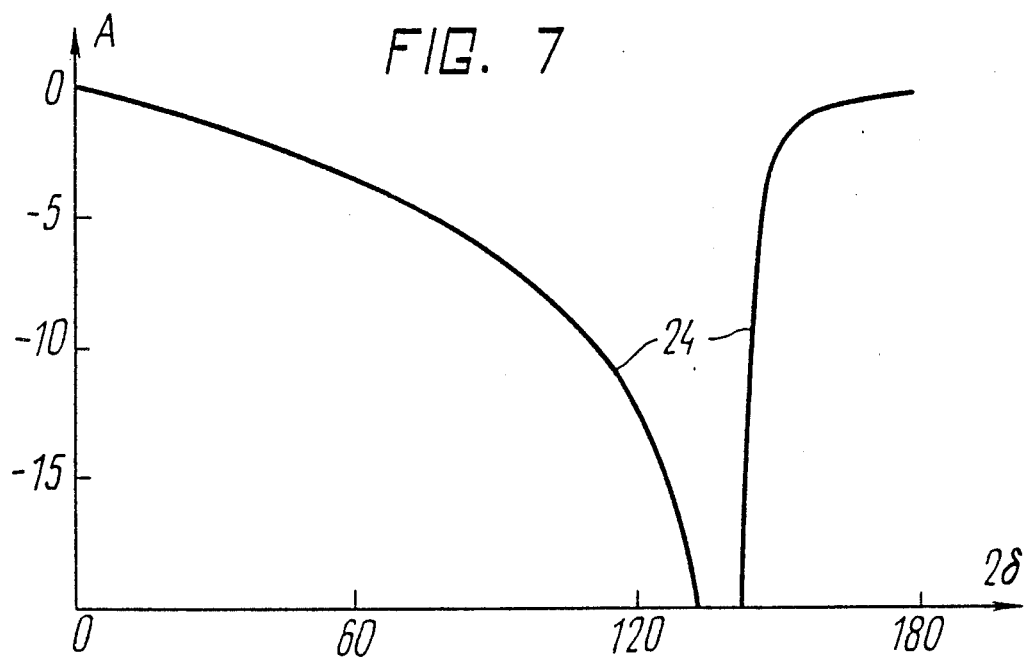
FIG. 8 presents a plot of dependence of the amplitude A of registered ultrasonic oscillations upon the angle $2\delta$, obtained in the arrangement of FIG. 6.

In the plots presented in FIGS. 7 and 8, the X-axis is calibrated in the values of the angles $2\delta$ (in degrees). The Y-axis in FIG. 7 is calibrated in the values of the angles $\xi_1=\xi_2=\xi$ (in degrees), and the Y-axis of FIG. 8 is calibrated in the values of the amplitude A of the registered transverse ultrasonic oscillations (in dB).

As illustrated by the curve 23 of FIG. 7 describing the dependence of $\xi$ on $2\delta$ for the specified value of $\alpha$, when the angle $\xi$ is selected in accordance with the disclosed method from the range $64° \leq \xi < 90°$, the angle $2\delta$ is selected from a range $0° \leq 2\delta \leq 60°$. Then the amplitude of the horizontally polarized component of the transverse ultrasonic oscillations incident upon the reflecting surface of the flaw 6 (FIG. 6) of the weld 4 of the article 2 would exceed the amplitude of the vertically polarized component at least twice, i.e. by 6 dB or more. As a result, as it can be seen from the curve 24 in FIG. 8, the amplitude A of the registered transverse ultrasonic oscillations is significantly greater than the amplitude of the transverse ultrasonic oscillations registered when $\xi=30°$ ($2\delta=130°$). As far as the area of the angles $2\delta > 130°$ is concerned, although the amplitude A of the registered oscillations in this area also exceeds the amplitude A with $\xi=30°$ ($2\delta=130°$) by 6 dB or more, this area of the values of the angles $2\delta$ would not be employed in practice for inspection of welds on account of the configuration of the weld 4 (FIG. 6) in the article 2 prohibiting such values of the angles $2\delta$ between the respective planes 3 and 8 of polarization of the radiated and registered ultrasonic oscillations.

Figure 9:
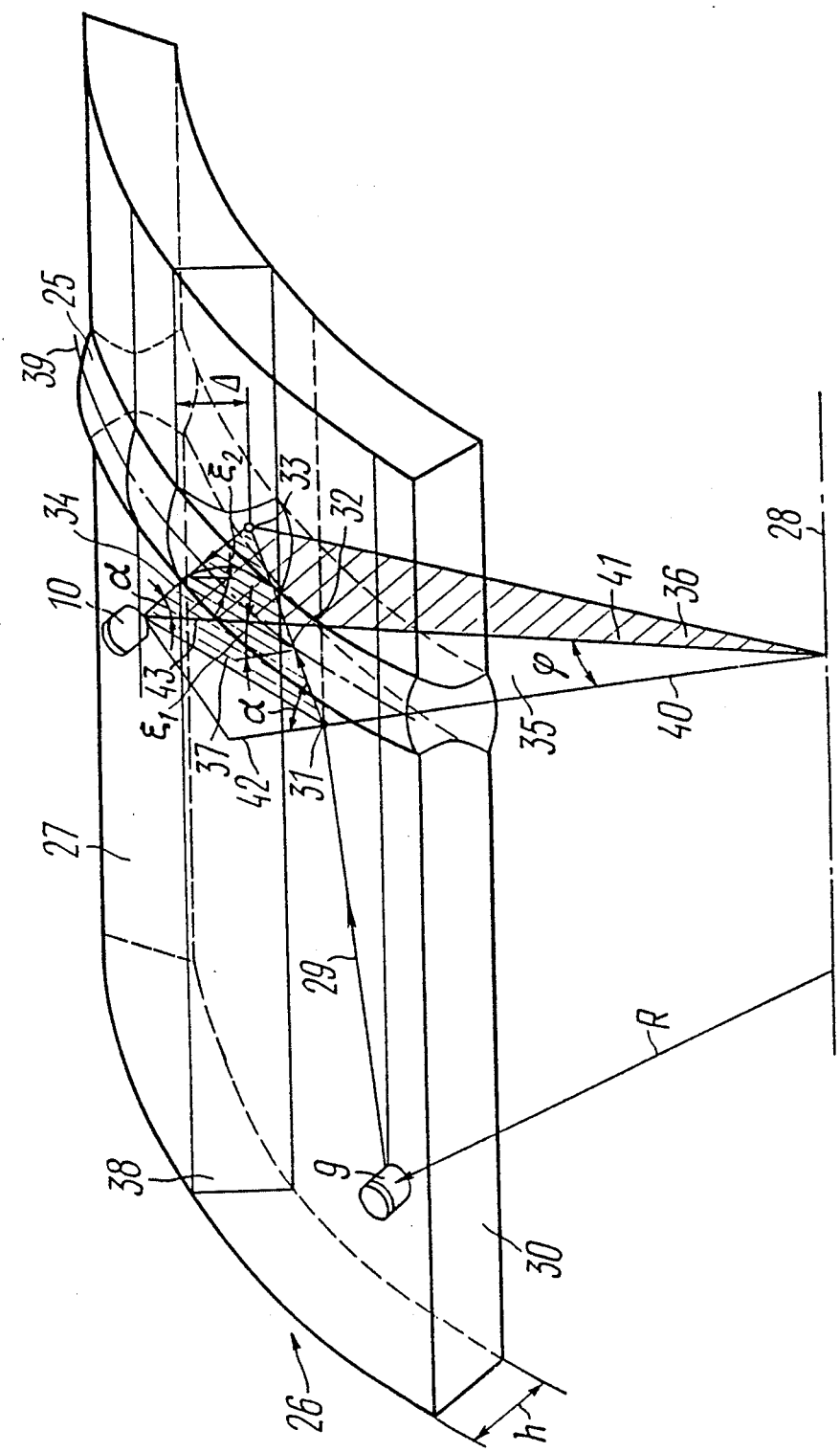
FIG. 9 illustrates schematically in a perspective view an arrangement for implementing yet another version of the method of ultrasonic inspection of welds of articles in accordance with the invention.
Figure 10:
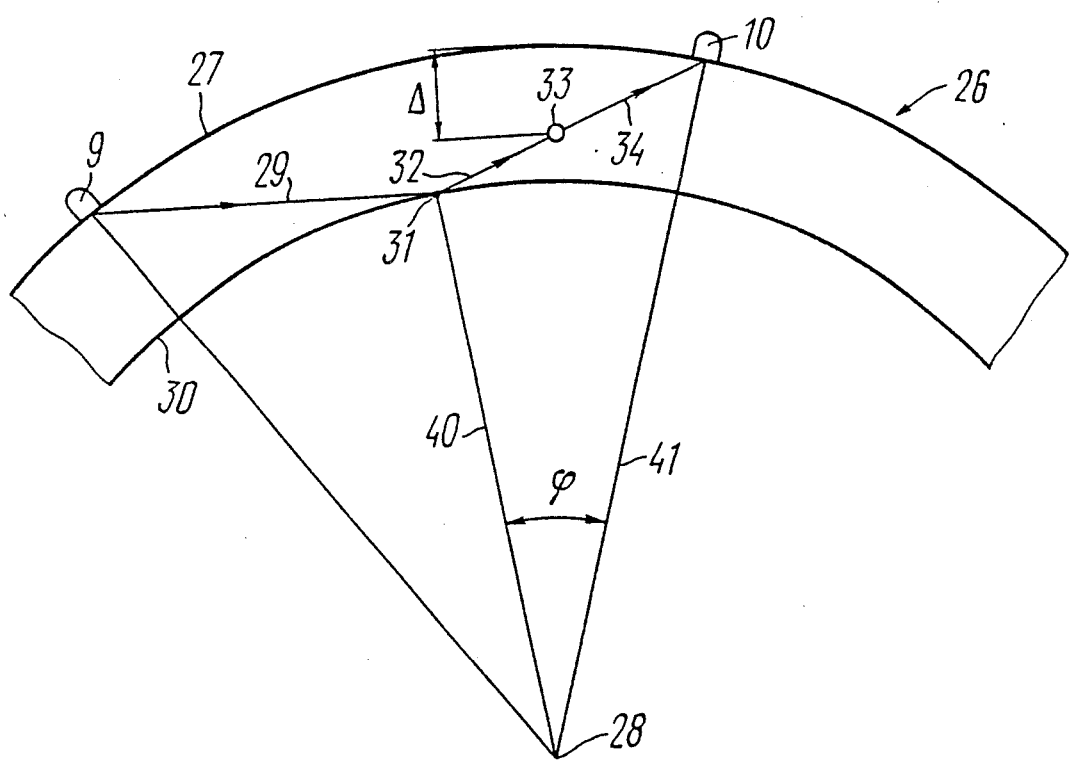
FIG. 10 is a side view on a larger scale of the arrangement of FIG. 9.

In still another arrangement for implementing the method in accordance with the present invention, illustrated in FIGS. 9 and 10, the method is employed for ultrasonic inspection of the weld 25 of an article 26 which is a pipe. In this case, too, the method performed in accordance with the present invention is basically similar to the method implemented by the arrangement of FIGS. 1 to 3.

The difference resides in the ultrasonic piezoelectric transducers 9 (FIGS. 9 and 10) and 10 being positioned on the outer cylindrical surface 27 of the article 26. The cylindrical surface 27 (FIG. 9) is described by a generatrix over a circle with a radius R from the longitudinal axis 28 of the pipe 26 whose wall thickness is h. Let us conditionally regard the article (pipe) 26 transparent.

Transverse ultrasonic oscillations radiated into the article 26 (FIGS. 9 and 10) by the piezoelectric transducer 9 through the surface 27 of the article 26 propagate in the radiating direction 29 and, upon their being reflected by the opposite inner wall (surface) 30 of the article 26 at a point 31, reach the reflecting surface of a flaw 33 of the weld 25 of the article 26 via a direction 32. Upon their mirror reflection by the reflecting surface of the flaw 33, they propagate in the direction 34 of mirror reflection and are registered by the ultrasonic piezoelectric detector 10.

Indicated with numerals 35, 36 and 37 in FIG. 9 are, respectively, the plane of polarization of the transverse ultrasonic oscillations radiated into the weld 25 of the article 26, the plane of polarization of the registered transverse ultrasonic oscillations and the plane of incidence of transverse ultrasonic oscillations upon the reflecting surface of the flaw 33 of the weld 25 of the article 26 (the planes 36 and 37 are differently shaded in the drawing for better clarity).

As it can be seen from FIG. 9, in accordance with the disclosed method, the respective directions 29 and 34 of transverse ultrasonic oscillations into the weld 25 of the article 26 and of mirror reflection of these oscillations by the reflecting surface of the flaw 33 of the weld 25 of the article 26 are situated outside a plane 38 perpendicular to the longitudinal axis 39 of the weld 25 of the article 26 and intersecting the reflecting surface of the flaw 33.

In the arrangement being described, the angle $2\delta$ between the respective planes 35 and 36 of polarization of the ultrasonic oscillations radiated into the article and of the registered ultrasonic oscillations are defined by locating the ultrasonic piezoelectric transducers 9 and 10 outside the plane 38, the respective positions of the transducers 9 and 10 in a projection belonging to the plane of the drawing of FIG. 10 being such that the angle $\psi$ between a radius vector 40 including the point 31 of reflection of ultrasonic oscillations by the inner cylindrical surface 30 and a radius vector 41 including the registering ultrasonic transducer 10 is selected to provide for $$\cos \psi = f(\alpha, \Delta, h, R),$$

where $\alpha$ is the angle between the direction 32 of radiation of ultrasonic oscillations into the weld 25 of the article 26 and a line 42 normal to the surface 27 of the article 26 at the point 31, equalling the angle $\alpha$ between the direction 34 of mirror reflection of the ultrasonic oscillations and a line 43 normal to the surface 27 of the article 26 at a point of location of the registering ultrasonic transducer 10; and $\Delta$ is the depth of occurrence of the flaw 33 in the weld 25 of the article 26.

Let us consider an example of implementing the disclosed method in detecting the flaw 33 (FIG. 9)—a spherical pore—in the weld 25—a welded joint of the steel pipe 26, with $\alpha = 70°$ and the ratio of the wall thickness h of the pipe 26 to its radius R being h:R=0.1 (R=1420 mm).

Figure 11:
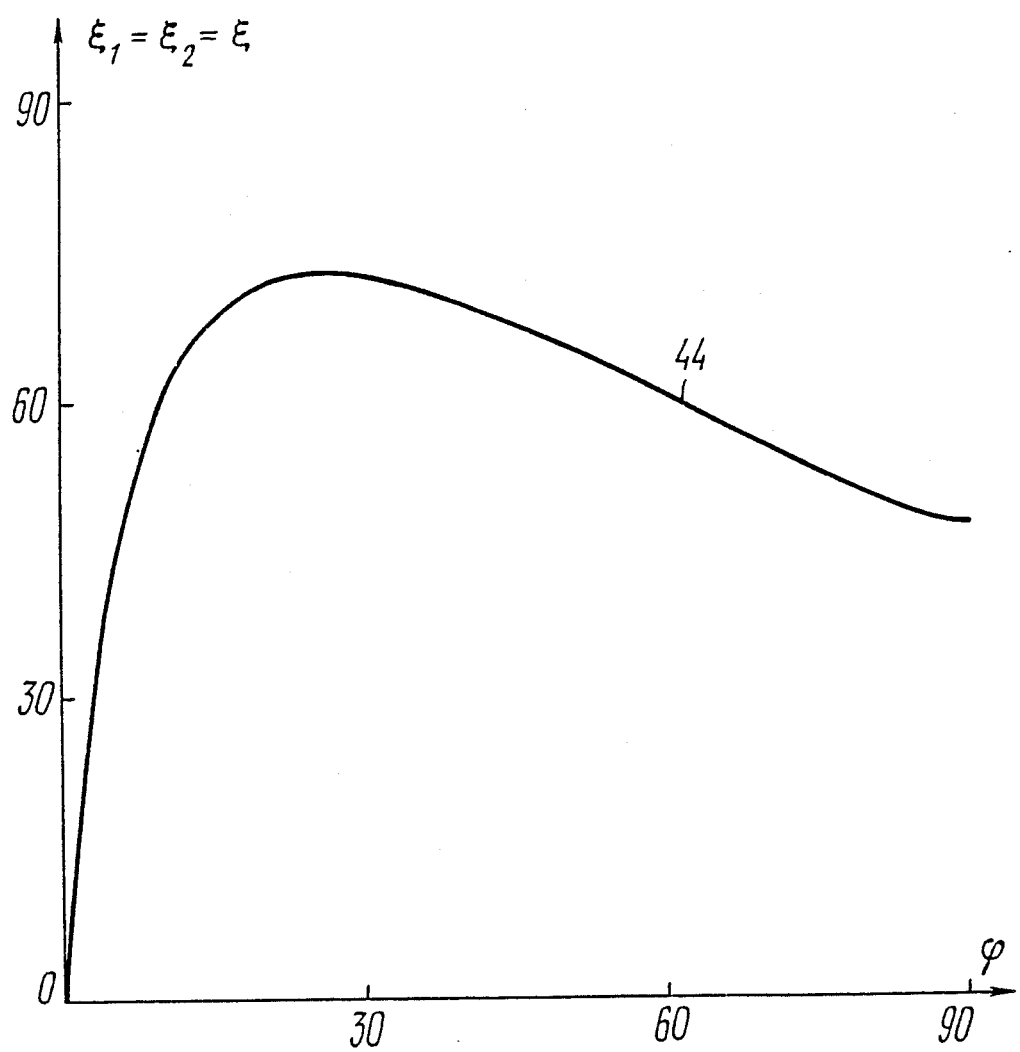
FIG. 11 presents a plot of dependence of the angle $\psi$ between a radius vector including the point of reflection of ultrasonic oscillations by the internal surface of the article and a radius vector including the registering piezoelectric transducer in a projection belonging to the plane of the drawing in FIG. 10 on the angle $\xi_1$ between the plane of polarization of transverse ultrasonic oscillations radiated into the weld of the article and the plane of incidence of these oscillations upon the reflecting surface of a flaw (or on the equal angle $\xi_2$ between the plane of polarization of the ultrasonic oscillations registered upon their reflection by the reflecting surface of the flaw and the plane of incidence of these oscillations upon the reflecting surface of the flaw, i.e. $\xi_1 = \xi_2 = \xi$).

In the plot presented by FIG. 11, the Y-axis is calibrated in the values of the angles $\xi_1 = \xi_2 = \xi$ (in degrees), and the X-axis is calibrated in the values of the angle $\psi$ (also in degrees).

It can be seen from the curve 44 in FIG, 11 that the condition $64° \leq \xi < 90°$ in accordance with the present invention is satisfied in the arrangement being discussed with $12° \leq \psi < 53°$. This provides for registering the horozontally polarized component in the ultrasonic oscillations reflected by the reflecting surface of the flaw 33 of the weld 25 of the article 26, which enhances the reliability of inspection of the weld 25.

The disclosed method of ultrasonic inspection of welds of articles provides for enhancing the reliability and credibility of the inspection procedure owing to the signal-to-noise ratio being enhanced by at least 6 dB. The disclosed method is implementable for inspection of a broad spectrum of articles including welded joints of small thickness and with great curvature of the surface. Moreover, the amplitudes of signals reflected by the flaws are close to the maximum theoretically attainable amplitudes, irrespective of the shape of a flaw to be detected.

Furthermore, the method in accordance with the invention allows to estimate the shape of a detected flaw with high credibility, i.e. to distinguish between three-dimensional and planar flaws from the results of the ultrasonic inspection procedure, and also to determine the orientation of planar flaws. This has been made possible by the selection of optimized directions of "sounding out" a flaw and by the capability of comparing ultrasonic oscillations scattered by the flaw in different directions.

INDUSTRIAL APPLICABILITY

The invention can be employed in various industries such as machine building, shipbuilding, nuclear power engineering, boiler-making, construction of gas and oil pipelines for ultrasonic inspection of welds in a broad spectrum of shapes and sizes.

We claim:

1. A method of ultrasonic inspection of welds of articles, including the steps of:

determining a direction of radiation of transverse ultrasonic oscillations into an article, a plane of polarization of said transverse ultrasonic oscillations radiated into a weld of said article, a plane of incidence of said transverse ultrasonic oscillations upon a reflecting surface of a flaw in said weld of said article, a direction of said transverse oscillations reflected from said reflecting surface of said welding flaw of said article, and a plane of polarization of said reflected transverse oscillations;

disposing said planes of polarization of said oscillations radiated into said weld of said article and reflected from said reflecting surface relative to each other at a preset angle of $2\delta$, determining this angle by disposing said direction of radiation of said oscillations into said weld and said direction of said reflected oscillations outside a plane perpendicular to a longitudinal axis of said weld and extending through said reflecting surface of said flaw, and by selecting an angle $\xi_1$ between said plane of polarization of said oscillations radiated into said weld of said article and said plane of incidence of said oscillations onto said reflecting surface and an angle $\xi_2$ between said plane of polarization of said reflected oscillations and said plane of incidence of said oscillations on said reflecting surface, either equal or in excess of 64° but less than 94°, thus extracting from said transverse ultrasonic oscillations a component horizontally polarized relative to said reflecting surface;

periodically radiating said transverse ultrasonic oscillations into said article and registering the time of arrival and the amplitude of said oscillations reflected from said reflecting surface at a preselected location; and using said horizontally polarized component extracted from said oscillations for estimation of the geometric size of said flaw, namely, the amplitude of said horizontally polarized component is used for estimation of said geometric size of said flaw while the time of its registration is used for locating said flaw in said weld.

2. A method of ultrasonic inspection of welds of articles according to claim 1, in which, in the case of ultrasonic inspection of welds of articles having a flat surface, through which said transverse ultrasonic oscillations are radiated into said article and registered after reflection from said reflecting surface, and a surface of an arbitrary shape placed opposite to said flat surface of the article;

said angle $\xi_1$ and said angle $\xi_2$ are equal to each other, i.e. $\xi_1 = \xi_2 = \xi$;

said angle $2\delta$ is selected from one of the relations;

$$2\delta = 2 \arccos \frac{1}{\sqrt{1 + \cos^2\alpha \tan^2\xi}}$$

or $$2\delta = 2 \arcsin \frac{1}{\sqrt{1 + \cos^2\alpha \tan^2\xi}}$$

where $\alpha$ is the angle between said direction of radiation into said article of said transverse ultrasonic oscillations and the normal to said flat surface of said article equal to angle $\alpha$ between said direction of said reflected oscillations and the normal to said flat surface of said article.

* * * * *